US006979669B2

(12) United States Patent
Raehse et al.

(10) Patent No.: US 6,979,669 B2
(45) Date of Patent: Dec. 27, 2005

(54) ENCAPSULATED ACTIVE INGREDIENT PREPARATION FOR USE IN PARTICULATE DETERGENTS AND CLEANING AGENTS

(75) Inventors: Wilfried Raehse, Duesseldorf (DE); Dieter Baur, Odenthal (DE); Werner Pichler, Kundl (AT)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 144 days.

(21) Appl. No.: 10/790,470

(22) Filed: Mar. 1, 2004

(65) Prior Publication Data

US 2004/0198629 A1 Oct. 7, 2004

Related U.S. Application Data

(63) Continuation of application No. PCT/EP02/09320, filed on Aug. 21, 2002.

(30) Foreign Application Priority Data

Aug. 30, 2001 (DE) ........................................ 101 42 124

(51) Int. Cl.$^7$ .......................... C11D 3/386; C11D 7/42; C11D 11/00; C12N 9/99

(52) U.S. Cl. ....................... 510/349; 510/376; 510/392; 510/441; 510/442; 252/186.25; 435/184

(58) Field of Search ................................ 510/349, 376, 510/392, 441, 442; 252/186.25; 435/184

(56) References Cited

U.S. PATENT DOCUMENTS

| | | | |
|---|---|---|---|
| 3,451,935 A | 6/1969 | Roald et al. | |
| 3,632,957 A | 1/1972 | Hannah | |
| 3,748,233 A | 7/1973 | Viccaro et al. | |
| 3,784,476 A | 1/1974 | van Kampen et al. | |
| 4,172,123 A | 10/1979 | Lowicki | |
| 4,264,738 A | 4/1981 | Stepanov et al. | |
| 4,266,031 A | 5/1981 | Tang et al. | |
| 4,751,003 A | 6/1988 | Raehse et al. | |
| 5,719,115 A | 2/1998 | Paatz et al. | |
| 6,224,274 B1 | 5/2001 | Nitsch et al. | |
| 6,270,690 B1 | 8/2001 | Himmrich et al. | 186/38 |
| 6,694,516 B1 | 2/2004 | Vandenabeele et al. | |

FOREIGN PATENT DOCUMENTS

| | | |
|---|---|---|
| CA | 2 304 033 | 3/1999 |
| DE | 1 803 099 | 5/1969 |
| DE | 1 617 118 | 2/1971 |
| DE | 1 617 190 | 2/1971 |
| DE | 1 617 232 | 2/1971 |
| DE | 1 940 488 | 2/1971 |
| DE | 2 044 161 | 4/1971 |
| DE | 17 67 568 | 7/1971 |
| DE | 17 92 074 | 10/1971 |
| DE | 2 032 768 | 1/1972 |
| DE | 2 137 042 | 2/1972 |
| DE | 2 137 043 | 2/1972 |
| DE | 2 201 803 | 7/1972 |
| DE | 2 121 397 | 11/1972 |
| DE | 25 48 344 A1 | 11/1976 |
| DE | 38 08 114 A1 | 9/1989 |
| DE | 40 14 055 A1 | 11/1991 |
| DE | 43 22 229 A1 | 1/1995 |
| DE | 195 06 004 A1 | 8/1996 |
| DE | 197 40 668 A1 | 3/1999 |
| DE | 197 40 669 A1 | 3/1999 |
| DE | 198 25 462 A1 | 12/1999 |
| EP | 0 006 638 B1 | 4/1984 |
| EP | 0 046 070 B1 | 6/1986 |
| EP | 0 168 526 B1 | 1/1989 |
| EP | 0 200 032 B1 | 7/1991 |
| EP | 0 407 189 A1 | 9/1991 |
| EP | 0 464 880 B1 | 12/1994 |
| EP | 1 213 344 A2 | 6/2002 |
| GB | 1 237 899 | 6/1971 |
| GB | 1 263 765 | 2/1972 |
| GB | 1 361 387 | 7/1974 |
| GB | 1 362 365 | 8/1974 |
| WO | WO 91/02792 A1 | 3/1991 |
| WO | WO 92/11347 A2 | 7/1992 |
| WO | WO 93/07260 A1 | 4/1993 |
| WO | WO 93/07263 A2 | 4/1993 |
| WO | WO 95/02031 A1 | 1/1995 |
| WO | WO 98/23719 A2 | 6/1998 |

OTHER PUBLICATIONS van Raay et al., "Zur Bestimmung der proteolytischen Aktivitat in Enzymkonzentraten und enzymhaltigen Wasch–, Spul– und Reinigungsmitteln", *Tenside*, vol. 7, pp. 125–132 (1970).

M. H. Abraham, "Solvent Effects on Transition States and Reaction Rates", Progr. Phys. Org. Chem., vol. 11, pp. 1–86 (1974).

Arnett et al., "Electronic Effects on the Menschutkin Reaction. A Complete Kinetic and Thermodynamic Dissection of Alkyl Transfer to 3– and 4–Substituted Pyridines", Journal of American Chemical Society, vol. 102, pp. 5892–5902 (1980).

*Primary Examiner*—Lorna M. Douyon
(74) *Attorney, Agent, or Firm*—Stephen D. Harper; Glenn E. J. Murphy

(57) ABSTRACT

A granulate for particulate detergents or cleaning agents, the granulate containing a detergent or cleaning agent active ingredient and an outer encapsulation layer formed of polyvalent metal salts of an unbranched or branched, unsaturated or saturated, mono- or polyhydroxylated fatty acid having at least 12 carbon atoms or a mixture of the salts. Also, a process for making the granulate by applying to the granules an encapsulation material that comprises one or more polyvalent metal salt or salts, preferably in the form of an aqueous dispersion in a fluidized bed process.

32 Claims, No Drawings

ENCAPSULATED ACTIVE INGREDIENT PREPARATION FOR USE IN PARTICULATE DETERGENTS AND CLEANING AGENTS

CROSS REFERENCE TO RELATED APPLICATIONS

This application is a continuation under 35 U.S.C. §365 (c) and 35 U.S.C. §120 of international application PCT/EP02/09320, filed Aug. 21, 2002. This application also claims priority under 35 U.S.C. §119 of DE 101 42 124.9, filed Aug. 30, 2001, each of which is incorporated herein by reference in its entirety.

BACKGROUND OF THE INVENTION

The invention relates to an encapsulated granulate which comprises a detergent or cleaning agent active ingredient, in particular an enzyme and/or a bleach activator, to a process for its preparation and to the use of the granulate in solid detergents and cleaning agents.

Besides the good washing and cleaning performance, the consumer expects modern detergents and cleaning agents to also have a positive esthetic impression which manifests itself, in particular, in a scent associated with freshness and cleanliness. In order to comply with this, the compositions normally comprise suitable fragrances. However, a not inconsiderable proportion of consumers disapprove, arguing, inter alia, that fragrances do not contribute to the washing or cleaning result, meaning that their use merely leads to an increase in the price of the compositions. These consumers prefer completely odorless detergents and cleaning agents. However, some ingredients of such compositions have a greater or lesser intrinsic odor which may also be based on minor components present in these ingredients. The use of such ingredients makes an unpleasant impression for fragrance-free compositions and, in the case of fragrance-containing compositions, may lead to an increase in the fragrance concentration in order to compensate for the intrinsic odor.

In connection with this problem, German patent application DE 17 92 074 discloses compositions which comprise zinc ricinoleate as deodorizing active ingredient, the deodorizing action of which is synergistically aided by the addition of other salts or esters of other saturated or unsaturated even-numbered or odd-numbered hydroxylated fatty acids having 17 or more carbon atoms, for example salts and esters of trioxystearic acids.

German patent application DE 25 48 344 discloses the deodorizing effectiveness of metal salts of an unsaturated fatty acid, in particular of metal ricinoleates. Metals from group II of the Periodic Table of the Elements and of the rare earths, such as cerium, lanthanum or neodymium, are preferred. Particular emphasis is given to zinc ricinoleate.

German patent application DE 38 08 114 relates to deodorizing active ingredient mixtures which comprise zinc ricinoleate and optionally the zinc salt of abietic acid and/or further zinc salts of other saturated or unsaturated hydroxylated fatty acids having 17 or more carbon atoms, partial esters of di- or polyhydroxyalkanes, mono- and disaccharides, polyethylene glycols or alkanolamines with the ene adducts of maleic anhydride to at least monounsaturated carboxylic acids having a chain length of from 10 to 25 carbon atoms with an acid number from 10 to 140, and optionally amino and/or amido compounds and remain in clearly dissolved form in preparations with water contents of up to 50% by weight.

Active ingredients which are customarily used in detergents and cleaning agents and in which the occurrence of a more or less unpleasant intrinsic odor cannot always be ruled out include, in particular, enzymes and bleach activators.

Enzymes, in particular proteases, are used extensively in detergents, washing auxiliaries and cleaning agents. Usually, the enzymes are used here not in the form of concentrates, but in mixtures with a dilution and carrier material. If such enzyme preparations are mixed into customary detergents, then a considerable decrease in the enzyme activity may arise upon storage, in particular when bleaching-active compounds are present. The application of the enzymes to carrier salts with simultaneous granulation according to German laid-open specification DE 16 17 190 or by pasting with nonionic surfactants according to German laid-open specification DE 16 17 118 or aqueous solutions of cellulose ethers according to German laid-open specification DE 17 87 568 does not lead to a noteworthy improvement in the storage stability since the sensitive enzymes in such mixtures are generally found on the surface of the carrier substance. Although the storage stability of the enzymes can be significantly increased by encapsulating the enzymes with the carrier material or embedding them into this and then converting them to the desired particle form by extrusion, compression and marumerization, as described, for example, in German patent specification DE 16 17 232, German laid-open specification DE 20 32 768, and the German published specifications DE 21 37 042 and DE 21 37 043. However, such enzyme preparations have only inadequate solubility properties. The undissolved particles can become entangled in the ware and soil it, or they are transferred to the waste-water unused. Although embedding agents known from German laid-open specification DE 18 03 099, which consist of a mixture of solid acids or acidic salts and carbonates or bicarbonates and decompose when water is added, improve the solubility capacity, they are for their part very sensitive to moisture and therefore require additional safety measures.

European patent specification EP 0 168 526 discloses enzyme granulates which comprise water-swellable starch, zeolite and water-soluble granulation auxiliaries. This document proposes a preparation process for such formulations which essentially consists in concentrating a fermenter solution freed from insoluble constituents, admixing said additives, granulating the resulting mixture and optionally encapsulating the granulate with film-forming polymers and dyes, The process with the additive mixture proposed therein is advantageously carried out with fermentation solutions which have been concentrated to a relatively high dry-substance content, for example 55% by weight. In addition, the granulates produced in this way have a sufficiently high rate of dissolution or disintegration under washing conditions that the granulates relatively rapidly disintegrate, sometimes even during storage, and the enzymes are deactivated.

International patent application WO 92/11347 discloses enzyme granulates for use in particulate detergents and cleaning agents which comprise 2% by weight to 20% by weight of enzyme, 10% by weight to 50% by weight of swellable starch, 5% by weight to 50% by weight of water-soluble organic polymer as granulation auxiliary, 10% by weight to 35% by weight of corn flour and 3% by weight to 12% by weight of water. As a result of such additives, the enzyme processing is possible without relatively large losses in activity.

International patent application WO 93/07263 discloses an enzyme-containing granulate which consists of a water-soluble or -dispersible core which is covered with a vinyl polymer, on which there is a layer of enzyme and vinyl polymer, where the granulate has an outer coating made of vinyl polymer. The outer coating may also comprise pigments. However, as a result of the multilayer construction, such an enzyme granulate is relatively complex to produce.

International patent application WO 93/07260 specifies various encapsulation materials for dust-free enzyme granulates which are produced by spraying a fermentation broth onto a hydratable carrier material. Fatty acid esters, alkoxylated alcohols, polyvinyl alcohol, polyethylene glycol, sugars and starch, inter alia, are listed as being suitable.

International patent application WO 95/02031 relates to an enzyme granulate comprising enzyme and inorganic and/or organic carrier material and a uniform outer pigment-containing encapsulation layer which is characterized in that the outer encapsulation layer consists of an encapsulation system which comprises 30% by weight to 50% by weight of a finely divided inorganic pigment, 45% by weight to 60% by weight of an alcohol which is solid at room temperature and has a melting point in the range from 45° C. to 65° C., up to 15% by weight, in particular 5% by weight to 15% by weight, of emulsifier for the alcohol, up to 5% by weight, in particular 0.2% by weight to 3% by weight of dispersant for the pigment and up to 3% by weight of water.

Even if the encapsulation systems described above are usually suitable for stably surrounding enzyme granulates such that no odor emerges from them, the aim is nevertheless to find alternatives, the use of which is as simple as possible and/or leads to cost advantages.

DESCRIPTION OF THE INVENTION

The present invention, which aims to make a contribution to this, relates to a granulate suitable for incorporation into particulate detergents or cleaning agents which comprises a detergent and/or cleaning agent active ingredient and has an outer encapsulation layer (coating) which is characterized in that the outer encapsulation layer comprises a polyvalent metal salt of an unbranched or branched, unsaturated or saturated, mono- or polyhydroxylated fatty acid having at least 12, in particular 16 to 24, carbon atoms or mixtures thereof. Among these, ricinoleic acid is particularly preferred. The granulate can be present in uncolored form or, for example as a result of the presence of pigment in the coating layer, white or colored.

Preferred polyvalent metals are chosen from the transition metals and the lanthanoids and are, in particular, the transition metals of groups IIB, VIIIB and optionally IB of the Periodic Table of the Elements, and also lanthanum, cerium and neodymium, particularly preferably cobalt, nickel, copper and zinc, zinc being the most preferred metal. Although the cobalt, nickel and copper salts and the zinc salts have similar effectiveness, the zinc salts are preferred for toxicological reasons. In a preferred embodiment, the encapsulation layer accordingly comprises one or more metal salts of ricinoleic acid, in particular zinc ricinoleate.

The encapsulation layer comprises one or more of said deodorizing active ingredients in an amount of usually 0.05% by weight to 5% by weight, preferably 0.1% by weight to 2.5% by weight, in particular 0.5% by weight to 2% by weight. In this connection it is preferred that the amount of the encapsulation material forming the encapsulation layer to be applied to the granulate is such that the resulting encapsulated granulate comprises 0.02% by weight to 1% by weight, in particular 0.05% by weight to 0.2% by weight, of said deodorizing active ingredient.

To solubilize the deodorizing active ingredient, the encapsulation material forming the encapsulation layer can comprise one or more solubility promoters, in particular in amounts of from 0.05% by weight to 5% by weight, preferably from 0.3% by weight to 1% by weight. Preferred solubility promoters are anionic, nonionic, cationic and/or amphoteric or zwitterionic surfactants, in particular anionic and/or nonionic surfactants with solubilizing, hydrotropic and/or emulsifying effect. The nonionic solubility promoters include unbranched or branched, saturated or unsaturated $C_{10-22}$-alcohols alkoxylated with ethylene oxide (EO) and/or propylene oxide (PO) and having an average degree of alkoxylation up to 30, preferably ethoxylated $C_{10-18}$-fatty alcohols with an average degree of ethoxylation of from 1 to 20, in particular 1 to 12, particularly preferably 1 to 8, most preferably 2 to 5, for example $C_{12-14}$-fatty alcohol ethoxylates with 2, 3 or 4 EO or a mixture of the $C_{12-14}$-fatty alcohol ethoxylates with 3 and 4 EO in the weight ratio of 1:1 or isotridecyl alcohol ethoxylate with 5, 8 or 12 EO, as are described, for example, in German patent specification DE 40 14 055, to which reference is made in this respect. Suitable anionic solubility promoters are, for example, the partial esters of di- or polyhydroxyalkanes, mono- and disaccharides, polyethylene glycols with the ene adducts of maleic anhydride onto at least monounsaturated carboxylic acids with a chain length of from 10 to 25 carbon atoms with an acid number of from 10 to 140, which are described in German patent application DE 38 08 114 and European patent application EP 0 046 070, to which reference is made in this respect. Besides an unbranched or branched, saturated or unsaturated, aliphatic or aromatic, acyclic or cyclic, optionally alkoxylated alkyl radical having 4 to 28, preferably 6 to 20, in particular 8 to 18, particularly preferably 10 to 16, most preferably 12 to 14, carbon atoms, preferred anionic solubility promoters have two or more anionic, in particular two, acid groups, preferably carboxylate, sulfonate and/or sulfate groups, in particular a carboxylate and a sulfate group. Examples of these compounds are the alpha-sulfo fatty acid salts, the acyl glutamates, the monoglyceride disulfates and the alkyl ethers of glycerol disulfate, and also the sulfosuccinamates, sulfosuccinamides and sulfosuccinates, The latter are the salts of the mono- and diesters of sulfosuccinic acid $HOOCCH(SO_3H)CH_2COOH$, while the sulfosuccinamates are understood as meaning the salts of the monoamides of sulfosuccinic acid, and sulfosuccinamides are understood as meaning the salts of the diamides of sulfosuccinic acid. The salts are preferably alkali metal salts, ammonium salts, and mono-, di- and trialkanolammonium salts, for example mono-, di- and triethanolammonium salts, in particular lithium, sodium, potassium or ammonium salts, particularly preferably sodium or ammonium salts, most preferably sodium salts. A preferred sulfosuccinate is sulfosuccinic lauryl polyglycol ester disodium salt.

In a particular embodiment, the encapsulation material comprises, as solubility promoter, one or more anionic and one or more nonionic surfactants, preferably in a weight ratio of the anionic to the nonionic surfactants of from 10:1 to 1:10, in particular 3:1 to 1:5, particularly preferably 1:1 to 1:3, most preferably from 1:1.5 to 1:2, where preferably the above-mentioned anionic and nonionic surfactants, in particular the sulfosuccinates, primarily the monoesters, and the alkoxylated $C_{10-22}$-alcohols, are combined with one another.

In a further preferred embodiment, the encapsulation material comprises one or more solubility promoters and one or more of said deodorizing active ingredients in a weight ratio of not more than 14:1, preferably from 10:1 to 1:10, in particular 5:1 to 1:5, particularly preferably 2:1 to 1:2, most preferably from 1.5:1 to 1:1.5, for example 1.3:1, 1.1:1, 1:1 or 1:1.1.

In a preferred embodiment, the encapsulation material forming the encapsulation layer additionally comprises one or more complexing agents. Complexing agents, usually also called sequesterants, are ingredients which are able to complex and deactivate metal ions in order to prevent their disadvantageous effects on the stability or the appearance of the compositions. In this connection, it is on the one hand important to complex the calcium and magnesium ions of water hardness which are incompatible with numerous ingredients of detergents and cleaning agents. The complexation of the ions of heavy metals, such as iron or copper, on the other hand, delays the oxidative decomposition of the finished compositions. Suitable are, for example, aminotrimethylenephosphonic acid, beta-alanine diacetic acid, ethylenediaminetetraacetic acid, citric acid, cyclohexanediaminetetraacetic acid, diethylenetriaminepentamethylenephosphonic acid, etidronic acid, gluconic acid, glucuronic acid, tetrahydroxyethylethylenediamine, tetrahydroxypropylethylenediamine, nitrilotriacetic acid and mixtures of these, where the acids among these may also be used in the form of their alkali metal and/or ammonium salts, Preferred complexing agents are tertiary amines, in particular tertiary alkanolamines (amino alcohols). These compounds have both amino and also hydroxy and/or ether groups as functional groups. Particularly preferred tertiary alkanolamines are triethanolamine and tetra(2-hydroxypropyl)ethylenediamine. Within the scope of the present invention, particularly preferred combinations of tertiary amines or tertiary alkanolamines with zinc ricinoleate and one or more ethoxylated fatty alcohols as nonionic solubility promoters, and optionally solvents are described in German patent specification DE 40 14 055, to which reference is made in this respect. The encapsulation material may, if desired, comprise complexing agents in an amount of usually up to 20% by weight, preferably 0.1 to 15% by weight, in particular 0.5 to 10% by weight.

A further preferred component of the encapsulation material is an alcohol with a melting point in the range from 45° C. to 65° C., which may optionally be present in amounts up to 60% by weight in the encapsulation material forming the encapsulation layer. This alcohol component is preferably a primary linear alcohol with 14 to 22 carbon atoms or a mixture of these. Said alcohols include, in particular, myristyl alcohol, cetyl alcohol, stearyl alcohol, arachidyl alcohol, behenyl alcohol and mono- to triunsaturated alcohols of corresponding chain length, it being essential that said alcohol component of the coating system has a melting point in the range from 45° C. to 65° C., in particular from 50° C. to 60° C., which should be understood as meaning here the temperature at which, upon heating, 100% of the alcohol component is present in liquid form. When using alcohol mixtures, it is also possible to use those which comprise small fractions, normally less than 15% by weight, based on the alcohol mixture, of fractions liquid at room temperature provided the total alcohol mixture appears solid at room temperature and has a solidification point in the range from 45° C. to 65° C., in particular from 50° C. to 60° C. The solidification point is the temperature at which, upon cooling material heated to a temperature of above the melting point, solidification occurs. It can be determined with the help of a rotating thermometer in accordance with the method of DIN ISO 2207. The use of polymeric diols with the given melting or solidification behavior is also possible, particular preference being given to polyethylene glycols.

In addition, the encapsulation layer may comprise inorganic pigment. Inorganic pigments with which possible troublesome colorations of the granulate can be covered include, for example, calcium carbonate, titanium dioxide, which may be present in rutile or anatase crystal modification, zinc oxide, zinc sulfide, white lead (basic lead carbonate), barium sulfate, aluminum hydroxide, antimony oxide, lithopones (zinc sulfide-barium sulfate), kaolin, chalk and/or mica, These are present in finely divided form such that they can be dispersed in a melt of the other constituents of the encapsulation material or in water. Usually, the average particle size of such pigments is in the range from 0.004 $\mu$m to 50 $\mu$m. Particularly when, in the course of the preparation of the encapsulated granulates, the pigment or the entire encapsulation material should be used in the form of an aqueous dispersion, it is preferred for this dispersion to comprise dispersants for the pigment. Such dispersants may be inorganic, for example aluminum oxide or silicon oxide, which may also serve as pigment, or organic, for example alkali metal carboxymethyl cellulose, diethylene glycol or dipropylene glycol. The use of pigments surface-modified with dispersants is likewise possible. Preference is given to using titanium dioxide pigment surface-modified with Al, Si, Zr or polyol compounds, in particular in rutile form, as is sold, for example, under the trade names Kronos® 2132 (Kronos-Titan) or Hombitan® R 522 (Sachtleben Chemie GmbH). It is also possible to use the Tiona® RLL, AG and VC grades from Solvay, and the Bayertitan® RD, R-KB and AZ grades from Bayer AG.

The invention further provides a process for the preparation of granulate suitable for incorporation into particulate detergents or cleaning agents which comprises a detergent and/or cleaning agent active ingredient and has an outer encapsulation layer which is characterized in that an encapsulation material is applied to the granulate as outer encapsulation layer which comprises a polyvalent metal salt of an unbranched or branched, unsaturated or saturated, mono- or polyhydroxylated fatty acid having at least 12 carbon atoms. Preferably, the content of said deodorizing active ingredient in the encapsulation material to be applied is 0.05% by weight to 5% by weight, in particular 0.3% by weight to 1% by weight.

In a preferred embodiment of the preparation process for a granulate according to the invention, the encapsulation material is applied in the form of an aqueous dispersion which, if desired, comprises up to 70% by weight, preferably 40% by weight to 60% by weight, of water in a fluidized bed of granulate to be encapsulated. The water introduced by the aqueous dispersion is removed again during simultaneous drying or drying which is subsequently required. In a further embodiment of the preparation process according to the invention, the encapsulation material, optionally with cooling, is applied to the granulate in the form of a heated liquid. Furthermore, a combination of these procedures, which consists in applying some of the encapsulation material in the form of an aqueous dispersion and some in the form of a melt is possible. Preferably, based on the finished granulate, 6% by weight to 15% by weight of the encapsulation material is applied as outer encapsulation layer to the granulate.

The detergent and/or cleaning agent active ingredient present in the granulate to be encapsulated is, in particular, one such ingredient which has a perceptible intrinsic odor. The encapsulation with said deodorizing active ingredient is particularly advantageously used with granulates which comprise enzyme and/or bleach activator.

Suitable enzymes are primarily the proteases, lipases, amylases and/or cellulases obtained from microorganisms, such as bacteria or fungi, preference being given to proteases obtained from Bacillus types, and their mixtures with amylases. They are obtained from suitable microorganisms in a known manner by fermentation processes which are described, for example, in German laid-open specifications DE 19 40 488, DE 20 44 161, DE 22 01 803 and DE 21 21 397, the US-American patent specifications U.S. Pat. No. 3,632,957 and U.S. Pat. No. 4,264,738, the European patent application EP 006 638, and the International patent application WO 91/2792. Enzymes are present in the granulates encapsulated according to the invention preferably in amounts of from 4% by weight to 20% by weight. If the enzyme granulate encapsulated according to the invention is a protease-containing formulation, the protease activity is preferably 150 000 protease units (PE, determined by the method described in Tenside 7 (1970), 125) to 350 000 PE, in particular 160 000 PE to 300 000 PE, per gram of enzyme granulate.

A preferred embodiment of the invention relates to a process for the preparation of an enzyme granulate suitable for incorporation into particulate detergents or cleaning agents and having an average particle size in the range from 0.4 mm to 1.2 mm, in particular from 0.8 mm to 1.2 mm, by extrusion of an enzyme premix produced by mixing a concentrated fermentation broth optionally freed beforehand from insoluble constituents by microfiltration, with inorganic and/or organic carrier material as additive, optional spheronization of the extrudate in a spheronizing device, drying and application of an outer encapsulation layer, where, in a fluidized bed of extrudate, an outer encapsulation layer is applied which comprises a polyvalent metal salt of an unbranched or branched, unsaturated or saturated, mono- or polyhydroxylated fatty acid having at least 16 carbon atoms.

Carrier materials which can be used for the enzyme are in principle all organic or inorganic pulverulent substances which do not destroy or deactivate the enzymes to be granulated, or destroy or deactivate them to a tolerably low degree and are stable under granulation conditions. Such substances include, for example, starch, corn flour, cellulose powder, alkali metal alumosilicate, in particular zeolite, sheet silicate, for example bentonite or smectite, and water-soluble inorganic or organic salts, for example alkali metal chloride, alkali metal sulfate, alkali metal carbonate or alkali metal acetate, sodium or potassium being the preferred alkali metals. Preference is given to using a carrier material mixture of water-swellable starch, corn flour and optionally cellulose powder, and alkali metal carbonate. The water-swellable starch is preferably corn starch, rice starch, potato starch or mixtures thereof, the use of corn starch being particularly preferred. Swellable starch is present in the enzyme granulates according to the invention preferably in amounts of from 20% by weight to 50% by weight, in particular from 25% by weight to 45% by weight. In this connection, the sum of the amounts of swellable starch and of the flour is preferably not more than 80% by weight, in particular 32% by weight to 65% by weight. The corn flour is, in particular, a product which can be prepared from wheat, rye, barley or oats, or is a mixture of these flours, preference being given to full-corn flour. A full-corn flour is understood here as meaning a not completely ground flour which has been produced from whole, unhusked grains or consists at least predominantly of such a product, the remainder consisting of completely ground flour or starch. Preference is given to using standard commercial wheat flour grades, such as Type 450 or Type 550. The use of flour products of the cereal types leading to abovementioned swellable starches is also possible if it is ensured that the flours have been prepared from the whole grains. As is known, as a result of the flour component in the additive mixture, a significant odor reduction of the enzyme preparation is achieved which far exceeds the odor reduction by incorporating similar amounts of appropriate kinds of starch.

Such grain flour is present in the enzyme granulates according to the invention preferably in amounts of from 10% by weight to 35% by weight, in particular from 15% by weight to 25% by weight. The enzyme granulates according to the invention can comprise, as further component of the carrier material, preferably 1% by weight to 50% by weight, preferably 5% by weight to 25% by weight, based on the total granulate of a granulation auxiliary system which comprises alkali metal carboxymethyl cellulose with degrees of substitution of from 0.5 to 1 and polyethylene glycol and/or alkyl polyethoxylate. Present in this granulation auxiliary system are preferably, in each case based on finished enzyme granulate, 0.5% by weight to 5% by weight of alkali metal carboxymethyl cellulose with degrees of substitution of from 0.5 to 1 and up to 3% by weight of polyethylene glycol and/or alkyl polyethoxylate, it being particularly preferred if at least 0.5% by weight, in particular 0.8% by weight to 2% by weight of polyethylene glycol with an average molar mass below 1 000 and/or alkyl polyethoxylate with at least 30 ethoxy groups is present if more than 2% by weight of alkali metal carboxymethyl cellulose is present. More highly substituted carboxymethyl cellulose, with degrees of substitution up to 3, is preferably not present in the granulation auxiliary system. In some cases, additional constituents of the granulation auxiliary system which may be used are also further cellulose or starch ethers, such as carboxymethyl starch, methylcellulose, hydroxyethylcellulose, hydroxypropylcellulose, and corresponding cellulose mixed ethers, gelatin, casein, tragacanth, maltodextrose, sucrose, invert sugar, glucose syrup or other water-soluble or readily dispersible oligomers or polymers of natural or synthetic origin. Synthetic water-soluble polymers which can be used are polyacrylates, polymethacrylates, copolymers of acrylic acid with maleic acid or compounds containing vinyl groups, and also polyvinyl alcohol, partially hydrolyzed polyvinyl acetate and polyvinylpyrrolidone. If said compounds are those with free carboxyl groups, they are normally present in the form of their alkali metal salts, in particular their sodium salts. Such additional granulation auxiliaries may be present in the enzyme granulates according to the invention in amounts up to 10% by weight, in particular from 0.5% by weight to 8% by weight. Higher molecular weight polyethylene glycols, i.e. those with an average molecular weight above 1 000, can be used as synthetic water-soluble polymers with dust-binding action, although the higher molecular weight polyethylene glycols in particular bring about an undesired increase in the required granulate dissolution time, meaning that these substances are preferably completely absent in enzyme granulates to be encapsulated according to the invention.

The enzyme granulates are preferably prepared from ferment broths, which are freed from insoluble accompanying substances, for example by microfiltration. The microfiltration here is preferably carried out as cross stream microfiltration using porous tubes with micropores greater than 0.1 μm, flow rates of the concentrate solution of more than 2 m/s and a pressure difference to the permeate side of less than 5 bar, as described, for example, in European patent application EP 200 032. The microfiltration permeate is then preferably concentrated by ultrafiltration, optionally with subsequent vacuum concentration. The concentration here can, as described in International patent application WO 92/11347, be carried out so as to arrive only at relatively low contents of dry substance of from preferably 5% by weight to 50% by weight, in particular from 10% by weight to 40% by weight. The concentrate is metered into a dry, pulverulent to granular mixture of the above-described additives which has expediently been prepared beforehand. The water content of the mixture should be chosen such that it can be converted, upon processing with stirring and beating tools, into granular particles which do not stick together at room temperature, and can be plastically deformed and extruded when higher pressures are applied. The flowable premix is then, in a manner known in principle, processed in a kneader and an attached extruder to give a plastic mass which is as homogeneous as possible, where, as a consequence of the mechanical processing, the mass can heat to temperatures between 40° C. and 60° C., in particular 45° C. to 55° C. The product leaving the extruder is passed through a perforated disk with subsequent chopping knife and thereby comminuted to cylindrical particles of a defined size, Expediently, the diameter of the bores in the perforated disk is 0.7 mm to 1.2 mm, preferably 0.8 mm to 1.0 mm. The particles present in this form can then be dried and encapsulated with the above-described encapsulation material. However, it has proven to be advantageous to spheronize the cylindrical particles leaving the extruder and chopper prior to encapsulation, i.e. to round and to trim them in suitable devices. Use is made for this purpose of a device which consists of a cylindrical container with stationary, solid side walls and a friction plate positioned in a rotatable manner on the base. Devices of this type are widespread in the art under the trade name Marumerizer® and described, for example, in German published specification DE 21 37 042 and DE 21 37 043. Any dust fractions with a particle size less than 0.1 mm, in particular less than 0.4 mm, and any coarse fractions with a particle size of above 2 mm, in particular above 1.6 mm which arise can then be removed by screening or air classification and in some cases be returned to the preparation process. After spheronization, the spheres are dried continuously or batchwise, preferably using a fluidized-bed drying plant, at inlet-air temperatures of from preferably 35° C. to 50° C. and in particular at a product temperature of not more than 42° C., to the desired residual moisture content of, for example, 4% by weight to 10% by weight, in particular 5% by weight to 8% by weight, based on the total granulate.

Further preferred detergent or cleaning agent ingredients which may be present in the granulate to be encapsulated are bleach activators, primarily from the substance classes of the N- or O-acyl compounds, for example polyacylated alkylenediamines, in particular tetraacetylethylenediamine, acylated glycolurils, in particular tetraacetylglycoluril, N-acylated hydantoins, hydrazides, triazoles, hydrotriazines, urazols, diketopiperazines, sulfurylamides and cyanurates, and also carboxylic anhydrides, in particular phthalic anhydride, carboxylic esters, in particular sodium nonanoyloxybenzenesulfonate, sodium isononanoyloxybenzenesulfonate and acylated sugar derivatives, such as pentaacetylglucose. Particularly preferred detergent or cleaning agent ingredients in this connection are bleach activators of the quaternized aminoalkylnitrile type of the general formula (I)

(I)

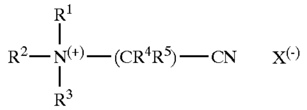

in which $R^1$ is —H, —$CH_3$, a $C_{2-24}$-alkyl or -alkenyl radical, a substituted $C_{2-24}$-alkyl or -alkenyl radical with at least one substituent from the group —Cl, —Br, —OH, —$NH_2$, —CN, an alkyl- or alkenylaryl radical with a $C_{1-24}$-alkyl group, or a substituted alkyl- or alkenylaryl radical with a $C_{1-24}$-alkyl group and at least one further substituent on the aromatic ring, $R^2$ and $R^3$, independently of one another, are chosen from —$CH_2$—CN, —$CH_3$, —$CH_2$—$CH_3$, —$CH_2$—$CH_2$—$CH_3$, —$CH(CH_3)$—$CH_3$, —$CH_2$—OH, —$CH_2$—$CH_2$—OH, —CH(OH)—$CH_3$, —$CH_2$—$CH_2$—$CH_2$—OH, —$CH_2$—CH(OH)—$CH_3$, —CH(OH)—$CH_2$—$CH_3$, —$(CH_2CH_2$—$O)_nH$ where n=1, 2, 3, 4, 5 or 6, $R^4$ and $R^5$, independently of one another, have a meaning given above for $R^1$, $R^2$ or $R^3$, and X is a charge-balancing anion. In some cases, the radicals $R^2$ and $R^3$ may also be part of a heterocycle including the N atom and optionally further heteroatoms, in particular a morpholine ring.

The preparation of compounds according to formula I can take place by known processes or in accordance with these, as have been published, for example, in European patent application EP 0 464 880, International patent application WO 98/23719, by Abraham in Progr. Phys. Org. Chem, 11 (1974), p. 1ff, or by Arnett in J. Am. Chem. Soc. 102 (1980), p. 5892ff. Preference is given to compounds according to formula I in which $R^1$, $R^2$ and $R^3$ are identical. Among these, particular preference is given to those compounds in which said radicals are methyl groups. On the other hand, preference is also given to those compounds in which at least 1 or 2 of said radicals are methyl groups, and the others have two or more carbon atoms. The anions $X^-$ include, in particular, the halides, such as chloride, fluoride, iodide and bromide, nitrate, hydroxide, phosphate, hydrogenphosphate, dihydrogenphosphate, pyrophosphate, metaphosphate, hexafluorophosphate, carbonate, hydrogencarbonate, sulfate, hydrogensulfate, $C_{1-20}$-alkyl sulfate, $C_{1-20}$-alkylsulfonate, optionally $C_{1-18}$-alkyl-substituted arylsulfonate, chlorate, perchlorate and/or the anions of $C_{1-24}$-carboxylic acids, such as formate, acetate, laurate, benzoate or citrate, alone or in any mixtures. Preference is given to bleach activators according to formula I in which $X^-$ is chloride, sulfate, hydrogensulfate, ethosulfate, $C_{12/18}$-, $C_{12/16}$ or $C_{13/15}$-alkyl sulfate, lauryl sulfate, dodecylbenzenesulfonate, toluenesulfonate, cumenesulfonate, xylenesulfonate or methosulfate or mixtures of these. Toluenesulfonate or cumenesulfonate are understood here as meaning the anion of the ortho, meta or paraisomers of methylbenzenesulfonic acid or isopropylbenzenesulfonic acid, respectively, and any mixtures thereof. Para-isopropylbenzenesulfonic acid is particularly preferred.

The bleach activators can, if desired, be converted into granular form prior to the encapsulation step essential for the invention, as described above for enzyme, the fermentation broth being replaced by an aqueous preparation of the bleach activator which arises as a result of the preparation. Bleach activator granulates encapsulated according to the invention have a content of bleach activator of preferably at least 40% by weight and in particular from 50% by weight to 92% by weight.

A preparation obtained by the process according to the invention consists of largely rounded, uniformly encapsulated and dust-free particles which generally have a bulk density of from about 500 to 900 grams per liter, in particular 650 to 880 grams per liter. The granulates according to the invention are characterized by very high storage stability, in particular at temperatures above room temperature and high atmospheric humidity, and rapid dissolution behavior in the wash liquor. Preferably, the granulates according to the invention release 100% of the activity of the active ingredient present therein, particularly when this is an enzyme, within 3 minutes, particularly within 90 seconds to 2 minutes, in water at 25° C.

The encapsulated granulate according to the invention or prepared according to the process of the invention is preferably used for the preparation of solid, in particular particulate, detergents or cleaning agents, which can be obtained by simply mixing the granulates with further particulate components customary in such compositions. For the incorporation into particulate detergents and cleaning agents, the granulate preferably has average particle sizes in the range from 0.8 mm to 1.2 mm. The granulates according to the invention preferably comprise less than 2% by weight, in particular at most 1.4% by weight, of particles with particle sizes outside the range from 0.4 mm to 1.6 mm. If desired, it is also possible to compress the encapsulated granulate according to the invention or prepared according to the process of the invention, optionally together with further ingredients of such compositions, to give a shape and, for example, to produce detergents and cleaning agents in tablet form or in the form of other moldings.

EXAMPLES

Example 1

A harvest slurry obtained after fermentation and comprising 75 000 protease units per g (PE/g), as described in International patent application WO 91/2792, was concentrated, following the removal of the fermentation residues, by decantation and microfiltration in an ultrafiltration plant. After further concentration by means of vacuum concentration, the aqueous enzyme suspension comprised 700 000 PE/g. This protease concentrate was mixed with additives (3.5% by weight sucrose, 4.5% by weight cellulose, 3% by weight carboxymethylcellulose with degree of substitution 0.65–0.75, 19% by weight of wheat flour, 35% by weight of corn starch and 3% by weight of polyethylene glycol, in each case based on the resulting mixture), homogenized and then converted to granulates in an extruder with cutting device. The hole diameter of the perforated plate of the extruder was 0.9 mm. The ratio of length to thickness of the granulate particle was 1. Following rounding and drying of the granulates, the particles with particle size less than 0.4 mm and greater than 1.6 mm were sieved off. The particle fraction between 0.4 mm and 1.6 mm was coated in a fluidized-bed spray granulator of the type STREA-1 from Aeromatic in the fluidized bed. During the coating, the following operating parameters were established:

| | |
|---|---|
| Inlet air temperature: | 85° C. |
| Product temperature: | 36° C. |
| Exit air temperature: | 33° C. |
| Amount of air: | 90 $m^3$/h |
| Throughput rate of coating suspension: | 8 g/min |

The coating suspension consisted of 16% by weight of titanium dioxide, 16% by weight of polyethylene glycol (PEG 12000), 1.5% by weight of a mixture of 50 parts by weight of zinc ricinoleate, 35 parts by weight of triple-ethoxylated lauryl alcohol and 15 parts by weight of tetra (2-hydroxypropyl)ethylenediamine (Tegosorb® conc 50), 0.5% by weight of sodium carboxymethylcellulose and the remainder to 100% by weight with water.

The coating suspension was sprayed onto the enzyme extrudate at the operating parameters given above, The water in the coating suspension evaporated and was discharged with the exit air. After spraying about 285 g of coating suspension per kg of enzyme granulate, the extrudates were encapsulated uniformly with a white color and protection layer. Compared with an otherwise unchanged granulate which was prepared by spraying on a coating suspension which lacked the mixture comprising zinc ricinoleate, the odor was significantly less, in particular the onion note of the odor was missing.

Example 2

A coating suspension consisting of titanium dioxide, polyethylene glycol and water was firstly sprayed onto the enzyme extrudate prepared as in example 1, and then the mixture given in example 1 of 50 parts by weight of zinc ricinoleate, 35 parts by weight of triple-ethoxylated lauryl alcohol and 15 parts by weight of tetra(2-hydroxypropyl) ethylenediamine was sprayed on, in each case in amounts such that the ratios of example 1 arose in the gross composition. Here too, the odor after spraying on the zinc ricinoleate was significantly less.

What is claimed is:

1. A granulate for incorporation into particulate detergents or cleaning agents, the granulate comprising a detergent or cleaning agent active ingredient and an outer encapsulation layer, wherein the outer encapsulation layer comprises a polyvalent metal salt of an unbranched or branched, unsaturated or saturated, mono- or polyhydroxylated fatty acid having at least 12 carbon atoms or a mixture of said salts, wherein the polyvalent metals are selected from the group consisting of transition metals and lanthanoids.

2. The granulate of claim 1, wherein the polyvalent metals are selected from the group consisting of transition metals of groups IIB, VIIIB, and IB.

3. The granulate of claim 1, wherein the polyvalent metal comprises cobalt, nickel, copper, or zinc.

4. The granulate of claim 1, wherein the fatty acid comprises ricinoleic acid.

5. The granulate of claim 1, wherein the encapsulation layer comprises the polyvalent metal salt or salts in an amount of from 0.05% by weight to 5% by weight.

6. The granulate of claim 5, comprising the polyvalent metal salt or salts in an amount of from 0.05% by weight to 1% by weight.

7. The granulate of claim 6, comprising the polyvalent metal salt or salts in an amount of from 0.05% by weight to 0.2% by weight.

8. The granulate of claim 5, wherein the encapsulation layer comprises one or more solubility promoters in amounts of from 0.05% by weight to 5% by weight.

9. The granulate of claim 8, wherein the encapsulation layer comprises one or more solubility promoters in amounts of from 0.3% by weight to 1% by weight.

10. The granulate of claim 8, wherein the solubility promoter comprises an unbranched or branched, saturated or unsaturated $C_{10-22}$-alcohol alkoxylated with ethylene oxide (EO) and/or propylene oxide (PO) and having an average degree of alkoxylation up to 30.

11. The granulate of claim 10, wherein the solubility promoter comprises an ethoxylated $C_{10-18}$-fatty alcohol with an average degree of ethoxylation of from 1 to 20.

12. The granulate of claim 10, wherein the ethoxylated $C_{10-18}$-fatty alcohol has an average degree of ethoxylation of from 2 to 5.

13. The granulate of claim 8, wherein the solubility promoter comprises an α-sulfo fatty acid salt, acyl glutamate, monoglyceride disulfate, an alkyl ether of glycerol disulfate, a sulfosuccinamate, sulfosuccinamide, and/or sulfosuccinate.

14. The granulate of claim 1, wherein the encapsulation layer comprises one or more complexing agents.

15. The granulate of claim 14, wherein the complexing agents comprise one or more tertiary alkanolamines.

16. The granulate of claim 1, wherein the encapsulation layer comprises one or more inorganic pigments.

17. The granulate of claim 1, comprising one or more enzymes.

18. The granulate of claim 17, comprising the one or more enzymes in amounts of from 4% by weight to 20% by weight.

19. The granulate of claim 17, wherein the enzyme comprise one or more of protease, lipase, amylase, and cellulase.

20. The granulate of claim 1, comprising at least 40% by weight of one or more bleach activators.

21. The granulate of claim 20, comprising from 50% by weight to 92% by weight of one or more bleach activators.

22. The granulate of claim 1, comprising one or more bleach activators of the general formula (I):

(I)

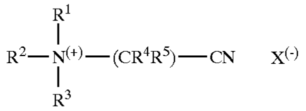

in which $R^1$ is —H, —$CH_3$, a $C_{2-24}$-alkyl or -alkenyl radical, a substituted $C_{2-24}$-alkyl or -alkenyl radical having at least one substituent from the group —Cl, —Br, —OH, —$NH_2$, —CN, an alkyl or alkenylaryl radical with a $C_{1-24}$-alkyl group, or is a substituted alkyl or alkenylaryl radical with a $C_{1-24}$-alkyl group and at least one further substituent on the aromatic ring, $R^2$ and $R^3$, independently of one another, are chosen from —$CH_2$—CN, —$CH_3$, —$CH_2$—$CH_3$, —$CH_2$—$CH_2$—$CH_3$, —$CH(CH_3)$—$CH_3$, —$CH_2$—OH, —$CH_2$—$CH_2$—OH, —CH(OH)—$CH_3$, —$CH_2$—$CH_2$—$CH_2$—OH, —$CH_2$—CH(OH)—$CH_3$, —CH(OH)—$CH_2$—$CH_3$, —$(CH_2CH_2$—$O)_nH$ where n=1, 2, 3, 4, 5 or 6, $R^4$ and $R^5$ independently of one another, have a meaning given above for $R^1$, $R^2$ or $R^3$, in some cases radicals $R^2$ and $R^3$ are also part of a heterocycle which includes the N atom and optionally further heteroatoms, and X is a charge-balancing anion.

23. The granulate of claim 22, wherein $R^2$ and $R^3$ form a morpholine ring.

24. A process for the preparation of granulate suitable for incorporation into particulate detergents or cleaning agents, comprising the steps of forming granules comprising a detergent or cleaning agent active ingredient and applying to the granules an encapsulation material that comprises one or more polyvalent metal salt or salts of an unbranched or branched, unsaturated or saturated, mono- or polyhydroxylated fatty acid having at least 12 carbon atoms to form an outer encapsulation layer on the granules, wherein the polyvalent metals are selected from the group consisting of transition metals and lanthanoids .

25. The process of claim 24, wherein the encapsulation material is applied to the granules such that the encapsulated granulate comprises 0.02% by weight to 1% by weight of the polyvalent metal salt or salts.

26. The process of claim 24, wherein the encapsulation material is applied to the granules such that the encapsulated granulate comprises 0.05% by weight to 0.15% by weight of the polyvalent metal salt or salts.

27. The process of claim 24, wherein the encapsulation material to be applied to the granules comprises 0.05% by weight to 5% by weight of the polyvalent metal salt or salts.

28. The process of claim 27, wherein the encapsulation material to be applied to the granules comprises 0.3% by weight to 1% by weight of the polyvalent metal salt or salts.

29. The process of claim 24, wherein the encapsulation material is applied in the form of an aqueous dispersion in a fluidized bed of granules to be encapsulated.

30. The process of claim 29, wherein the encapsulation material comprises up to 70% by weight of water.

31. The process of claim 30, wherein the encapsulation material comprises 40% by weight to 60% by weight of water.

32. The process of claim 24, wherein the granule to be encapsulated comprises an enzyme and/or bleach activator.

* * * * *